US009008274B2

(12) United States Patent
Stevens et al.

(10) Patent No.: US 9,008,274 B2
(45) Date of Patent: Apr. 14, 2015

(54) SYSTEMS AND METHODS FOR SELECTING IMAGE DISPLAY PARAMETERS

(71) Applicant: General Electric Company, Schenectady, NY (US)

(72) Inventors: Grant Morey Stevens, Cedarburg, WI (US); Roy A. Nilsen, Waukesha, WI (US); Brian William Thomsen, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 246 days.

(21) Appl. No.: 13/726,398

(22) Filed: Dec. 24, 2012

(65) Prior Publication Data

US 2014/0177803 A1    Jun. 26, 2014

(51) Int. Cl.
*A61B 6/00* (2006.01)
*G06T 11/00* (2006.01)
*G06F 19/00* (2011.01)
*A61B 6/03* (2006.01)

(52) U.S. Cl.
CPC . *A61B 6/52* (2013.01); *A61B 6/032* (2013.01); *A61B 6/461* (2013.01); *A61B 6/5294* (2013.01)

(58) Field of Classification Search
CPC ........ A61B 6/032; A61B 6/482; A61B 6/461; A61B 6/507; A61B 6/542; G06T 11/005; G06F 19/321; G06F 19/3406
USPC .............. 378/4, 8, 91, 98; 600/425; 382/130, 382/131, 195
See application file for complete search history.

(56) References Cited

U.S. PATENT DOCUMENTS

| | | | |
|---|---|---|---|
| 6,185,271 B1 * | 2/2001 | Kinsinger | 378/19 |
| 6,256,364 B1 * | 7/2001 | Toth et al. | 378/4 |
| 6,775,352 B2 | 8/2004 | Toth et al. | |
| 7,489,799 B2 * | 2/2009 | Nilsen et al. | 382/100 |
| 7,688,938 B2 | 3/2010 | Paliwal et al. | |
| 7,734,006 B2 | 6/2010 | Miyazaki et al. | |
| 7,774,040 B1 * | 8/2010 | Dutta et al. | 600/407 |
| 7,813,471 B2 | 10/2010 | Hirokawa et al. | |
| 8,184,775 B1 * | 5/2012 | Fan et al. | 378/147 |
| 8,280,137 B2 * | 10/2012 | Hsieh et al. | 382/131 |
| 8,311,181 B2 * | 11/2012 | Thomsen et al. | 378/5 |
| 2005/0031082 A1 | 2/2005 | Haaga et al. | |

(Continued)

FOREIGN PATENT DOCUMENTS

JP          4964062 B2    1/2008
WO    WO 2011008967 A1    1/2011

*Primary Examiner* — David A Vanore
(74) *Attorney, Agent, or Firm* — Dean Small; The Small Patent LAw Group, LLC

(57) ABSTRACT

An imaging system includes an identification module, a determination module, and a display module. The identification module is configured to identify one or more first scanning parameters and one or more first display parameters corresponding to a first image, and to identify one or more second scanning parameters corresponding to scanning information acquired during a second scan. The determination module is configured to determine, based on the one or more first scanning parameters and the one or more second scanning parameters, one or more second display parameters so that the scanning information acquired during the second scan may be used to provide a second image appearing more similar to the first image. The display module is configured to use the one or more second display parameters to provide the second image configured to be displayed to a viewer.

21 Claims, 4 Drawing Sheets

(56) References Cited

U.S. PATENT DOCUMENTS

| | | |
|---|---|---|
| 2007/0147579 A1 | 6/2007 | DeMan et al. |
| 2010/0131885 A1* | 5/2010 | Licato et al. .................. 715/781 |
| 2010/0310144 A1* | 12/2010 | Chen et al. .................... 382/131 |
| 2011/0142315 A1* | 6/2011 | Hsieh et al. ................... 382/131 |
| 2011/0150171 A1* | 6/2011 | Breuer et al. ..................... 378/4 |
| 2011/0317806 A1 | 12/2011 | Eusemann et al. |
| 2012/0114093 A1 | 5/2012 | Yu et al. |
| 2013/0105699 A1* | 5/2013 | Asma et al. .............. 250/363.03 |
| 2014/0056497 A1* | 2/2014 | Hsieh et al. ................... 382/131 |
| 2014/0093031 A1* | 4/2014 | Flohr ................................ 378/8 |
| 2014/0098932 A1* | 4/2014 | Profio et al. .................... 378/19 |
| 2014/0177788 A1* | 6/2014 | Stevens et al. ................. 378/16 |
| 2014/0177803 A1* | 6/2014 | Stevens et al. ................. 378/98 |
| 2014/0270439 A1* | 9/2014 | Chen ............................ 382/131 |
| 2014/0355857 A1* | 12/2014 | Grosskopf et al. ............ 382/131 |

* cited by examiner

SYSTEMS AND METHODS FOR SELECTING IMAGE DISPLAY PARAMETERS

BACKGROUND OF THE INVENTION

The subject matter disclosed herein relates generally to imaging systems and methods, and more particularly, to systems and methods for selecting image display parameters for imaging.

Computed Tomography (CT) imaging systems typically include an x-ray source and a detector. As the x-rays pass from the source through the object being imaged, the x-rays become attenuated before impinging upon the detector. The intensity of the attenuated beam radiation received at the detector is responsive to the attenuation of the x-rays by the object, with detector elements producing separate electrical signals responsive to the beam attenuation at the detector element location. These electrical signals may be referred to as x-ray attenuation measurements. Further, the x-ray source and the detector array may be rotated around the object to be imaged such that an angle at which an x-ray beam intersects the object changes. A group of x-ray attenuation measurements, or projection data, from a detector at one gantry angle may be referred to as a "view." A set of views made at different gantry angles during one revolution of an x-ray source and detector may be referred to as a "scan." In an axial scan, projection data is processed to construct an image that corresponds to a two-dimensional cross-section or slice of an object being scanned An image may be reconstructed, for example, using a technique referred to as a "filtered back-projection technique." This process converts the attenuation measurements from a scan into discrete integers called "CT numbers" or "Hounsfield Units" (HU). These HU's are used to control the brightness of a corresponding pixel on a cathode ray tube or a computer screen display in a manner responsive to the attenuation measurements. This integer conversion, or scoring, allows a physician or a technician to determine the approximate density of matter based on the intensity of the computer display.

Various parameters describing or defining an image being acquired may be adjusted, for example, to reduce a dosage level, to account for a smaller object being imaged (such as a smaller patient such as an infant or child), to account for a change in image reconstruction technique (e.g., a different type of software), or the like. However, when parameters at which a scan is performed (and/or corresponding to the reconstruction of an image) change, the appearance of an image produced based on the scan may change. Even if image quality is maintained, the image may appear differently than an image expected by a practitioner, resulting in potential confusion to a practitioner, inconvenience to a practitioner, lack of confidence in a diagnosis made using the image, or the like.

BRIEF DESCRIPTION OF THE INVENTION

In one embodiment, an imaging system is provided. The imaging system includes an identification module, a determination module, and a display module. The identification module is configured to identify one or more first scanning parameters and one or more first display parameters corresponding to a first image. In some embodiments, the first image may not necessarily be actually acquired, reconstructed, or displayed. For example, the first image may be a theoretical construct that is not actually required, reconstructed, or displayed. The identification module is also configured to identify one or more second scanning parameters corresponding to scanning information acquired during a second scan. The determination module is configured to determine, based on the one or more first scanning parameters and the one or more second scanning parameters, one or more second display parameters used to display the second image, wherein the second image is displayed having an apparent image quality more similar to an apparent image quality of the first image than if displayed using the one or more first display parameters. The display module is configured to use the one or more second display parameters to provide the second image configured to be displayed to a viewer.

In another embodiment, a method (e.g., a method for displaying results of a scan) is provided. The method includes identifying one or more reference scanning parameters and one or more reference display parameters corresponding to a reference image for a reference scan. The method also includes identifying one or more second scanning parameters corresponding to scanning information acquired during a second scan. Further, the method includes determining, based on the one or more reference scanning parameters and the one or more second scanning parameters, one or more second display parameters used to display the second image, wherein the second image is displayed having an apparent image quality more similar to an apparent image quality of the first image than if displayed using the one or more first display parameters. Also, the method includes using the one or more second display parameters to provide the second image configured to be displayed to a viewer.

In a further embodiment, a tangible and non-transitory computer readable medium is provided. The tangible and non-transitory computer readable medium includes one or more computer software modules configured to direct a processor to identify one or more reference scanning parameters and one or more reference display parameters corresponding to a reference image for a reference scan. The one or more computer software modules are also configured to direct a processor to identify one or more second scanning parameters corresponding to scanning information acquired during a second scan. Further, the one or more computer software modules are configured to direct a processor to determine, based on the one or more reference scanning parameters and the one or more second scanning parameters, one or more second display parameters used to display the second image, wherein the second image is displayed having an apparent image quality more similar to an apparent image quality of the first image than if displayed using the one or more first display parameters. The one or more computer software modules are further configured to direct a processor to use the one or more second display parameters to provide the second image configured to be displayed to a viewer.

DETAILED DESCRIPTION OF THE INVENTION

Figure 1:
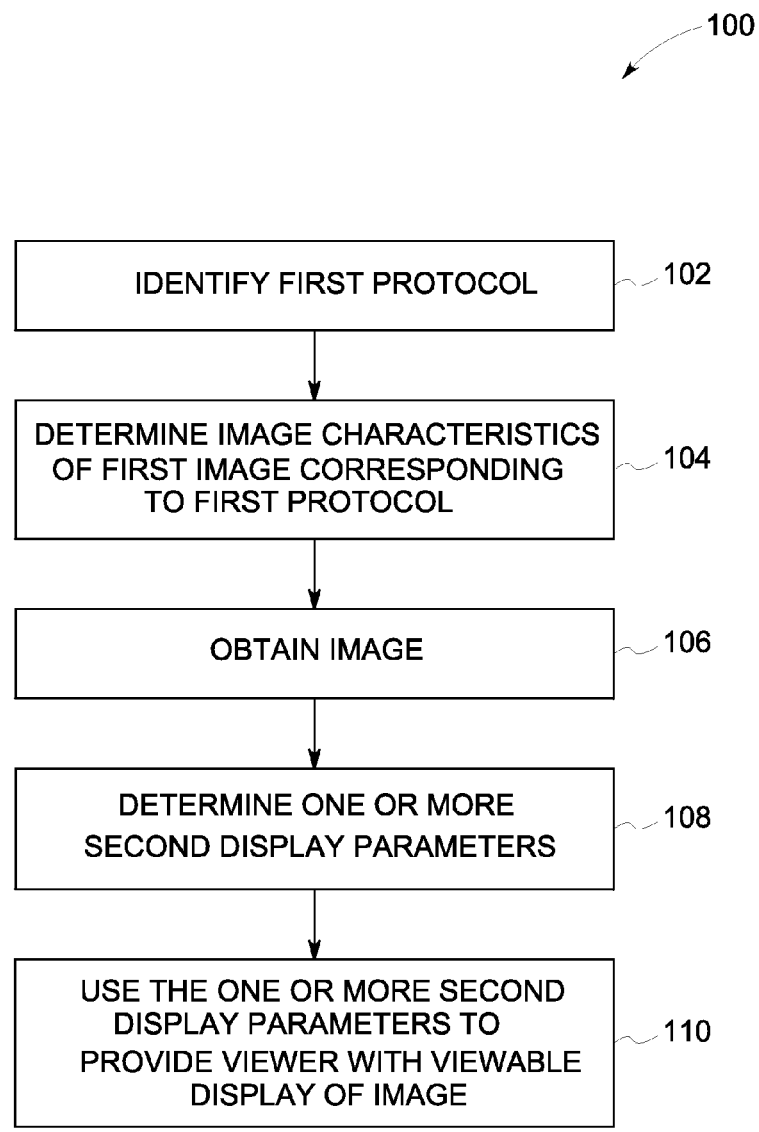
FIG. 1 is a flowchart of an exemplary method for displaying an image of an object in accordance with various embodiments.

The following detailed description of various embodiments will be better understood when read in conjunction with the appended drawings. To the extent that the figures illustrate diagrams of the functional blocks of the various embodiments, the functional blocks are not necessarily indicative of the division between hardware and/or circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings.

Described herein are various embodiments, for example, for selecting (e.g., autonomously selecting) display parameters for a second image so that the second image has an overall appearance (e.g., apparent image quality or other characteristic) similar to a first image. For example, a practitioner may input a reference protocol specifying or corresponding to scanning parameters for acquiring scanning information and/or reconstructing an image using acquired scanning information, as well as display parameters for displaying an image reconstructed based on the scanning parameters of the reference protocol. Based on use of the reference protocol in the past or other past experience, the practitioner may have an expectation of an overall image appearance corresponding to the reference protocol. Images that deviate from this expectation may reduce a practitioner's comfort level in analyzing such images, reduce a practitioner's ability to accurately analyze such images, require additional steps by a user to modify image display parameters, and/or reduce a level of confidence in a diagnosis based on analysis of the image. However, one or more of the scanning parameters specified by the reference protocol may be deviated from in performing a scan and/or reconstructing an image. While such a deviation may not necessarily impair the usefulness of a resulting image (and, in some cases, may even enhance the usefulness of a resulting image), an image obtained using such different scanning parameters and displayed using the display parameters specified by or corresponding to the reference protocol may present an unfamiliar or unexpected appearance to the practitioner, for example due to relative brightness levels, amounts or rates of gradation between shades of grey in an image, or the like. Various embodiments provide for an automatic determination of one or more display parameters so that an image obtained using one or more scanning parameters that deviate from a reference protocol is presented to a viewer having an overall appearance conforming to, approximating, or approaching the overall appearance of an image corresponding to the reference protocol.

A technical effect of at least one embodiment includes improved consistency in the presentation of scanning results to practitioners. Also, a technical effect of at least one embodiment includes improved convenience to practitioners analyzing images acquired using scanning techniques that differ in one or more respects from a reference protocol to which the practitioners may be accustomed. Further, a technical effect of at least one embodiment includes improvement of ease of use of image display and/or adjustment to one or more scanning or display parameters. A technical effect of at least one embodiment includes the reduction or elimination of time, expense, and/or radiation exposure associated with repeated image acquisition or reconstruction necessitated by lack of practitioner comfort with or confidence in an image that does not satisfy expectations regarding appearance. A technical effect of at least one embodiment includes the display of a reconstructed image having one or more image quality characteristics and/or an overall appearance tailored for particular practitioners (e.g., based on equipment used by the practitioners, individual preferences of practitioners or groups of practitioners, or the like).

FIG. 1 is a flowchart of a method 100 for reconstructing an image of an object in accordance with various embodiments. Although the method 100 is described in a medical setting using a Computed Tomography (CT) imaging system, it is contemplated that the benefits of the various embodiments described herein may accrue to all x-ray or ionizing radiation based imaging systems, such as x-ray, dual energy x-ray absorptiometry (DEXA), vascular, interventional, fluoroscopy, or the like. The method 100, for example, may also be employed in the context of industrial CT imaging systems such as a baggage scanning CT system typically used in a transportation center such as, for example, but not limited to, an airport or a rail station. The method 100, for example, may employ structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion.

At 102, a first protocol is identified. The first protocol may specify, define, or otherwise include first scanning parameters (e.g., parameters relating or corresponding to the operation or performance of a scan during which information used to reconstruct an image may be collected and/or the reconstruction of the image) and first display parameters (e.g., parameters relating or corresponding to the display of an image corresponding to the scan). The protocol may be a reference protocol referring to a standard employed by a practitioner or group of practitioners, or to a sample or example scan performed in past that is known to have provided usable or acceptable results. Thus, the first scan need not necessarily be performed (or the first image necessarily reconstructed) as part of the method 100, but instead may provide a reference or baseline level or measure of overall appearance and/or image quality along with associated parameters. The first scanning parameter may include or correspond to one or more of a tube voltage setting (or a projected monochromatic tube voltage for embodiments employing dual energy scanning), tube current, presence, type, and/or amount of contrast agent, image reconstruction technique, or the like.

The first display parameter may include one or more of window level, window width, or the like. Window level may be understood as the midpoint or point along a brightness or contrast continuum (expressed, for example, in terms of Hounsfield Units (HU) or CT number) about which a display is centered, and window width as a measure of a range of contrast or brightness levels included in the display on either side of the center or midpoint. Pixels having a brightness within the range defined by the window width centered about the window level may appear as varying shades of grey (depending on the particular brightness of a given pixel), while pixels outside of the range defined by the window width centered about the window level will either appear as black or white (depending on which side of the range a given pixel falls). For example, in some embodiments, pixels with relatively higher CT numbers (e.g., corresponding to bone) may appear white, pixels with relatively lower CT numbers (e.g., corresponding to lungs or other structures including or filled with air) may appear black, and pixels with intermediate CT numbers (e.g., soft tissues, fat, or the like) may appear as shades or gradations of grey. By selecting appropriate window widths and levels, an image may be presented in a way that is clear to a viewer, and provides an increased or maximum amount of information to a viewer. For example, portions of a region of interest may be depicted as varying shades of grey, allowing a viewer to discriminate between different aspects of a region of interest.

Consider for example, a single pixel having a CT number of about 100. The pixel will appear brighter (e.g., a shade of grey closer to white than black) in a display having a window level of 80 when compared to a display having a window level of 1200 (assuming large enough window widths to include the pixel). By knowing a range of CT numbers for the pixels corresponding to an image, an appropriate window level and window length may be chosen to include all or a desired portion of the pixels within a range depicted by varying shades of grey. A window level may be chosen to provide a center point of a range at a desired value, while the window width may be chosen to provide a desired level of coverage and detail. For example, a generally narrower (e.g., smaller) width may be selected to accentuate differences between pixels having relatively close CT numbers, but an overly narrow width may result in an overly large amount of pixels being depicted as white and/or black. Further, a generally wider (e.g., larger) width may provide a larger number of pixels provided with a shade of grey instead of black or white, but an overly wide width may tend to provide an image that makes distinctions between pixels having relatively close CT numbers difficult to discern, or having a "washed out" appearance. In some embodiments, a first scanning parameter such as tube voltage or current and/or a first display parameter such as window width or window length may be manually input by an operator instead of being identified via a specified protocol. In still other embodiments, some parameters may be individually input while other parameters are identified via an identified protocol.

The reference protocol may correspond to a standard protocol that may be defined by a particular user. For example, a practitioner or group of practitioners may define a standard protocol for a given scan "X" as having a tube voltage of 120 kv, a tube current of 80 mA, a window width of 100 HU and a window level of 35 HU (e.g., a range of 100 HU centered about 35 HU, or a window beginning at −65 HU and extending to 135 HU). Thus, a practitioner may provide an input indicating that a scan of type "X" will be performed, and the various parameters may be identified based on the identification of scan type "X." The scan type may correspond to a portion of the anatomy (e.g., head, abdomen), to a portion of the anatomy along with a purpose of the scan (e.g., a scan of a patient chest to determine a fluid level, a scan of a patient abdomen to identify a lesion), or the like. The parameters associated with the identified protocol provide a baseline that may be used to understand practitioner expectations for the appearance of an image. The protocol may also specify or otherwise have associated therewith various image quality metrics, such as an amount of image contrast, a noise level, a contrast to noise ratio (CNR), or the like.

As indicated above, a protocol (or one or more parameters) may be identified based, for example, on a user input, a determination made autonomously in response to a user input, or a combination thereof. In various embodiments, the user input may be input via use of a keypad, dial, touchscreen, or the like that allows a user to specify a particular protocol or a particular value of one or more parameters, such as voltage, current, noise index, window level, window width, or the like. Alternatively or additionally, a user may be presented with a series of values for a particular parameter from which a selected value may be chosen. For example, a user may be presented with a choice between various tube voltage settings or stations (e.g., a user may select one of a 80 kV setting, a 100 kV setting, a 120 kV setting, or a 140 kV setting). It may be noted that different voltage settings may be provided in other embodiments, while a continuous or essentially continuous variation in voltage levels may be provided in still other embodiments. As another example, a user may be presented with a choice of various protocols.

By way of example, tube voltages in some embodiments may range between about 80 kV to about 140 kV. Tube current may vary from about 10 mA to about 800 mA. A noise index may range from about 5 to about 100. For example, a reference setting including a tube voltage of about 120 kV and a noise index of about 13 may be input by a user. (A tube current may be determined based on the noise index.) A window level may range from about −1024 to +3071 HU. The ranges discussed herein are intended by way of example, and are not intended to limit or exclude the use of different parameters or ranges in other embodiments.

At 104, image characteristics of the first, reference, or baseline image are determined. The image characteristics may be based on qualities or characteristics of interest or deemed important by physicians (e.g., as learned in clinical studies or other research). Further, particular characteristics or qualities of interest may vary by procedure (e.g., type of tissue being scanned or purpose of scan), equipment (e.g., type of software used during image reconstruction), individual user preferences (e.g., particular preferences of a given user regarding, for example, desired amount of gradation in shade between particular structures or tissue types), or the like, so that the particular image characteristics identified may vary by procedure, equipment, user, or the like. Thus, an image characteristic or quality (along with a corresponding adjustment to image appearance) may be customized or tailored for a particular situation and/or user. Image characteristics may include or otherwise correspond to one or more of CT number, Noise Index, Contrast to Noise Ratio (CNR), or the like. Image characteristics may include an average or mean CT number (and/or position of an average or mean CT number for an image along the range provided by the window width corresponding to the image), a shade for one or more pixels corresponding to one or more tissue types and/or anatomical landmarks in an image, a standard deviation of CT numbers or other statistical measure of a distribution, additional characterization of the range of CT numbers in an image, or the like.

In some embodiments, a histogram may be employed to identify one or more image characteristics or qualities of a first or reference image, and/or to describe or characterize an overall image appearance (e.g., apparent image quality). A histogram may be understood as a running total of brightness in an image, for example, providing a mapping, charting, or other description or depiction of the distribution of pixels across a range of shades in an image. For example, a histogram or other distribution model may indicate, tabulate or describe how many (or what percentage or proportion) of pixels in an image are black, how many are white, how many are grey (or particular shades of grey). The relative similarities between information that may be contained in the histograms of a reference image and a second image (e.g., similarities in types or numbers of shades, amount of gradation between shades, distribution of pixels among shades, or the like in the histograms) may be used in some embodiments as a measure of similarity in overall appearance or apparent image quality. Using information from the histogram, a model or other description of a reference image may be constructed, such as via an automatic image analysis.

At 106, an image is obtained. For example, contrast agent may be introduced into a patient (if applicable), and a scan (e.g., a CT scan) performed to acquire scanning information, and an image reconstructed using the scanning information. In the depicted embodiment, the scan is performed using second scanning parameters that are different from the first or reference scanning parameters. For example, one or more of a tube voltage, tube current, noise index, bowtie filter, field of view, image reconstruction approach or technique, or the like may differ for the scan performed at 106 from a corresponding value for the first or reference protocol. In some embodiments, the second scanning parameters that differ from the reference protocol may be automatically selected. A user may input the reference protocol, and one or more scanning parameters may be autonomously adjusted by a scanning system, for example to reduce a radiation dosage or the like. The system may alert the user of changes to scanning parameters that are made in some embodiments, and not alert the user in other embodiments. Thus, a user may or may not be aware that scanning parameters different from a reference or user entered protocol have been used to obtain an image. In some embodiments, a change to one or more scanning parameters from a reference protocol may be specified by a user or made responsive to a user input. For example, a user may enter a reference protocol, and then enter one or more specific values to change one or more scanning parameters. As another example, a user may enter a reference protocol, and also enter additional information about the scan to be performed, such as that the scan will be taken of an infant, a child, a patient of a given size, or the like. The scanning system may then automatically adjust one or more scanning parameters (e.g., to reduce a tube voltage for a small patient) responsive to the user entry of the additional information.

Thus, for example, one or more scanning parameters used to acquire scanning information and/or reconstruct an image may differ for that called for by a reference protocol. For example, one or more of a tube voltage, tube current, presence, number, or type of bowtie filter, or the like used during scanning may differ from a reference protocol. Further, a reconstruction technique used to reconstruct an image using the information acquired during a scan may change, for example due to a change or update in software used to process scanning information. As another example, in embodiments utilizing dual energy scanning, a reference protocol may call for an image to be reconstructed corresponding to a first monochromatic voltage, and the image may be reconstructed corresponding to a second monochromatic voltage that is different from the first monochromatic voltage.

Because one or more scanning parameters used to obtain the image at 106 differ from scanning parameters corresponding to the reference protocol, the image obtained at 106 may differ in appearance from an image corresponding to the reference protocol if displayed using similar display parameters. An image appearance may change even if an image quality metric such as CNR remains the same. For example, in situations where the image contrast increases along with the noise, the CNR may be maintained, but a resulting image may appear noisier (as well as brighter). Thus, a practitioner used to seeing a particular image type or appearance provided by the reference protocol may be confused, uncomfortable, or the like when presented with an image that differs from the reference protocol. A practitioner may be particularly surprised, uncomfortable, or the like in situations where the scanning parameters were adjusted autonomously or otherwise without the knowledge or awareness of the practitioner.

Various embodiments provide for the selection or determination of display parameters that differ from display parameters corresponding to a reference protocol to display an image (e.g., the image obtained at 106) in a way that makes the image appear more similar to the reference image (e.g., an image corresponding to the reference protocol).

At 108, one or more second display parameters are determined. The second display parameters may be determined based on the one or more reference scanning parameters and the one or more second scanning parameters. For example, a second display parameter used to display an image obtained at 106 may be determined based on a difference between a reference scanning parameter and a corresponding second scanning parameter. In the depicted embodiment, the one or more second display parameters are selected or determined so that the second image may be displayed appearing more similar (e.g., having a similar apparent image quality) to the reference image than if the second image were displayed using the one or more first display parameters. Examples of second display parameters include window level, window width, or the like.

In some embodiments, a second display parameter (or parameters) may be determined by an adjustment to a reference display parameter using a change in one or more scanning parameters. For example, in some embodiments, a second display parameter may be determined using a formula as follows: $D_{image} = D_{ref} + A*\Delta S1 + B*\Delta S2$, where $D_{image}$ is a given display parameter used to display an image (e.g., an image obtained at 106 using second scanning parameters), $D_{ref}$ is the display parameter value corresponding to the first or reference protocol, A is a first coefficient (e.g., a coefficient determined experimentally, for example in clinical studies), $\Delta S1$ is the change in a first scanning parameter (e.g., tube voltage) from the first or reference protocol to the value used in obtaining the image, B is a second coefficient, and $\Delta S2$ is the change in a second scanning parameter (e.g., tube current) from the first or reference protocol to the value used in obtaining the image. The above format of the relationship is provided by way of example and not limitation, as other formats or mathematical expressions may be used in various embodiments.

In various embodiments, the format of the formula, values of coefficients, numbers of parameters employed, types of parameters employed, or the like may vary. For example, in some embodiments, a given display parameter may be determined based on the variation of a single given scanning parameter. For example, it may be noted that window level (and/or image contrast or brightness) and tube voltage may be relatively closely correlated. Thus, a change in window level from a reference window level may be determined using a change in tube voltage. Thus, in some embodiments, a second window level for displaying an image obtained using a second tube voltage may be expressed as $WL = WL_{ref} + C*(TV - TV_{ref})$, where WL is the window length used to display the image, $WL_{ref}$ is the window length corresponding to the reference protocol, C is a coefficient (e.g., experimentally determined, determined in clinical studies, or the like), TV is the tube voltage used during acquisition of scanning information used to reconstruct the image (e.g., the second tube voltage), and $TV_{ref}$ is the tube voltage corresponding to the reference protocol.

As another example, it may be noted that window width (and/or image noise) and tube current may be correlated. Thus, a change in window width from a reference window width may be determined using a change in tube current. Thus, in some embodiments, a second window width for displaying an image obtained using a second tube current may be expressed as $WW=WW_{ref}+D*(TC-TC_{ref})$, where WW is the window width used to display the image, $WW_{ref}$ is the window width corresponding to the reference protocol, D is a coefficient (e.g., experimentally determined, determined in clinical studies, or the like), TC is the tube current used during acquisition of scanning information used to reconstruct the image (e.g., the second tube current), and $TC_{ref}$ is the tube current corresponding to the reference protocol. It may be noted that window width may also be considered as being impacted primarily by noise, which may be based on voltage, current, slice width, rotation speed, reconstruction algorithm, or the like. Thus, in some embodiments, a change in window width may correspond to a change in tube current while also taking into account one or more other factors that may impact noise as well.

Thus, in some embodiments, a window width and/or a window level used to display an image may be determined based on changes in one or more scanning parameters used to obtain an image from corresponding values of a reference protocol. For example, for a reference protocol calling for a window width of 400 HU and a window level of 40 HU, an image obtained using different scanning parameters than the reference protocol values may be displayed using a window width of 500 HU and a window level of 50 HU to account for varying brightness and noise in the obtained image from an image obtained using the reference protocol, and to display the image in a manner that will appear more similar to a practitioner to a reference image.

It should be noted that the particular formula or relationship between changes in scanning parameters and corresponding changes in display parameters may vary case by case. Different formula formats, different values of coefficients, or the like may be employed as appropriate. Further, a lookup table or tables may be employed additionally or alternatively to a formula. The formula, table, or other relationship between changes in scanning parameters and corresponding changes in display parameters may vary, for example, based on one or more of type of scan, type of tissue or portion of anatomy being scanned, purpose of scan, individual user preferences, equipment used to perform scan and/or to reconstruct an image, or the like.

A given particular relationship may be determined experimentally, for example, in clinical studies. For example, different factors that may affect user perception of an image, such as image contrast, noise, or the like, along with display parameters such as window level, window width, or the like may be varied, along with scanning parameters, to provide a series of data points identifying images that appear similarly (based on observer opinion, objective image characteristic metrics, or a combination thereof). Once a sufficient amount of data points are collected for a given scanning technique or mode, a relationship correlating changes in display parameters to changes in scanning parameters may be defined. In various embodiments, the amount of adjustment and/or an absolute value of a parameter may be based on a predominant material in a region of interest, a material of most interest in a region of interest, a weighted combination, or the like. Further, materials not necessarily present in a region of interest in a scan, such as mathematical or otherwise modeled materials may also be used in determining one or more display parameters in various embodiments.

Additionally or alternatively, a histogram of the second image may be studied and/or adjusted to conform to or otherwise approach a histogram of a reference image. For example, a histogram of an image obtained using the second scanning parameters and displayed using display parameters of the reference protocol may be compared to a histogram of a reference image. If the histogram of the second image has too many or too few of one or more colors or shades (e.g., white, black, various shades of grey) in comparison to the reference histogram, one or more display parameters for the second image may be adjusted to provide a histogram more closely approximating the histogram of the reference image. Such a comparison and adjustment may be done as part of a clinical study to identify or quantify the similarity of appearance of images, and/or may be performed as part of an adjustment to reference parameters to provide display parameters for a particular image.

In some embodiments, a histogram comparison may be used in conjunction with a defined relationship between scanning and display parameters. For example, an initial set of second display parameters may be determined using an adjustment to reference display parameters using a defined relationship based on a change of second scanning parameters relative to reference scanning parameters as discussed herein. Then, an initial display image may be provided using the initial set of second display parameters. A histogram of the initial display image may be compared to a reference image, and additional adjustments to the initial set of second display parameters may be made, as appropriate, to provide a final display image that may be provided to a user. Thus, a histogram comparison may be used to fine tune a displayed image before presentation to a user.

As another example, an average or mean CT number may be used as one example of an image characteristic, and a second window level and width set so that the average or mean CT number appears in the same relative position within a window (e.g., has a same or similar shade) in the second image as in the first image. Alternatively or additionally, a particular shade may be identified for one or more portions of interest in a reference image (e.g., anatomical landmarks in a region of interest). The window width and window level for displaying the second image may be selected to provide an image with each portion of interest having the same or otherwise corresponding shade in the second image as in the reference image. Alternatively or additionally, a standard deviation of CT number, a range of CT numbers, noise measurement, or the like may be be used as examples of image characteristics.

Thus, in various embodiments, display parameters may be adjusted from a reference value based on a predetermined or otherwise defined relationship between one or more changes in scanning parameters and one or more changes in display parameters to obtain a desired appearance, for example an appearance that will be generally familiar to a practitioner. In embodiments, display parameters, such as window width and window level, thus may be determined relative to a user preference or expectation to reduce, minimize, or eliminate the impact of changes in image acquisition or reconstruction technique on image appearance. For example, increasing window width may reduce the conspicuity of noise in a displayed image. Such a change may also reduce the apparent image contrast. In some embodiments, the image contrast may have been increased (e.g., via a change in one or more scanning parameters such as voltage), thus mitigating the apparent reduction in image contrast. Further, window level may also be adjusted to address any apparent reduction in contrast.

At 110 the second display parameters are used to provide a user with a viewable display of the second image (e.g., an image obtained at 106.) The viewable or displayed image may be provided as one or more of a display on a computer or other screen, a printout, or the like.

Thus, various embodiments provide for display of a second image to have a similar apparent image quality to a first image even though the second image was acquired via a scan taken at different settings. In various embodiments, an image obtained by a scan may have an overall appearance or apparent image quality approximating or corresponding to a reference image to which a user is accustomed, providing improved convenience to the user in analyzing the image as well as improved confidence in any diagnoses made using the image, even though the image was obtained using scanning parameters that differ from a reference protocol used to produce or otherwise associated with the reference image. In some embodiments, a user need not necessarily be aware that any adjustments to scanning and/or display parameters from a reference protocol entered or identified by the user have been changed. For example, as also discussed in connection with FIG. 2 below, a user may input a reference protocol, a scanning system may autonomously adjust scanning parameters used to acquire scanning information and/or reconstruct an image, and the system may autonomously adjust display parameters used to display the image so that the image is presented to the user having an appearance generally similar to a reference image corresponding to the reference protocol input by the user.

Figure 2:
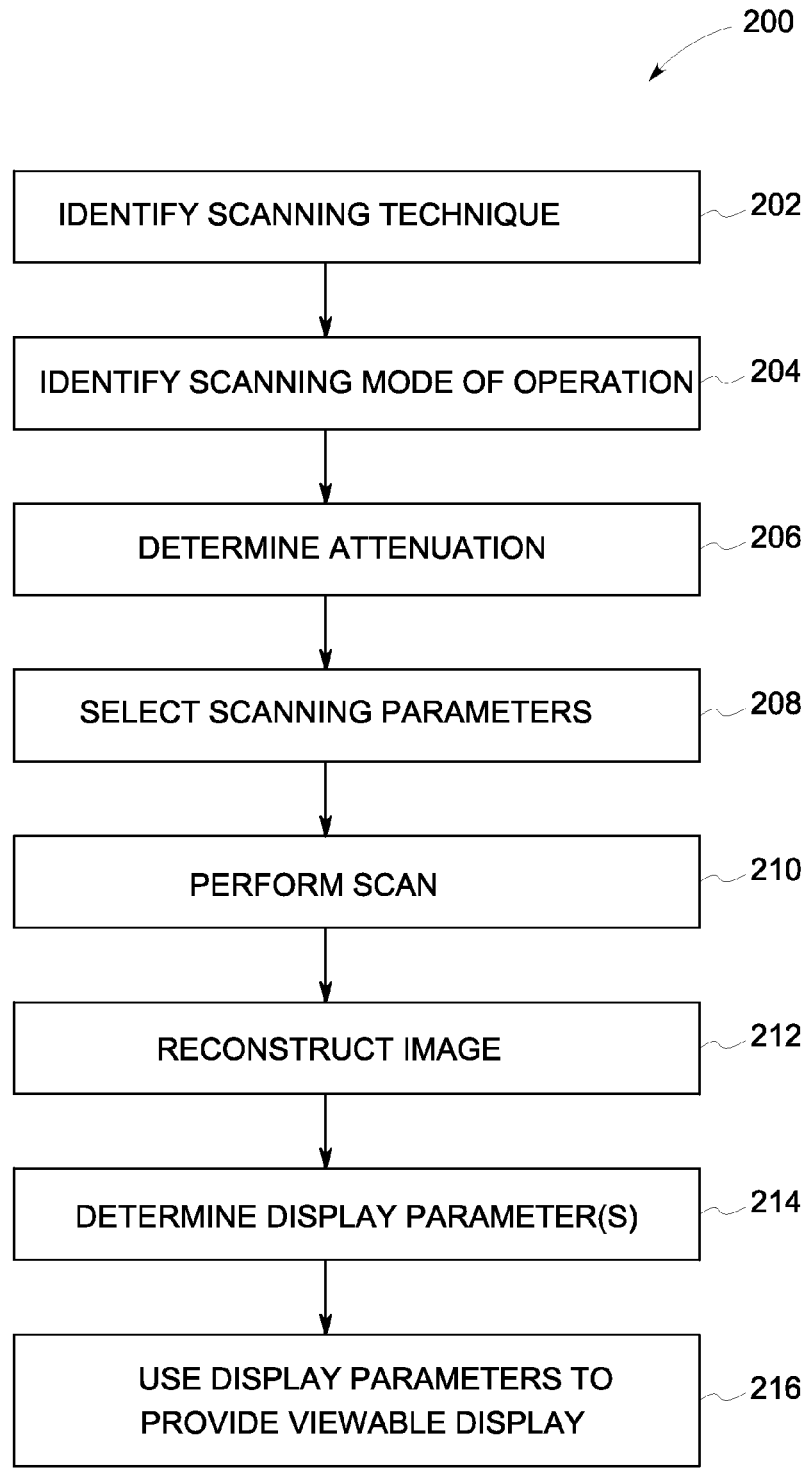
FIG. 2 is a flowchart of an exemplary method for reconstructing and displaying an image of an object in accordance with various embodiments.

FIG. 2 is a flowchart of a method 200 for reconstructing and displaying an image of an object in accordance with various embodiments. Although the method 200 is described in a medical setting using a Computed Tomography (CT) imaging system, it is contemplated that the benefits of the various embodiments described herein may accrue to all x-ray or ionizing radiation based imaging systems. The method 200, for example, may employ structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion.

At 202, a scanning technique is identified. For example, the scanning technique may be a reference scanning technique corresponding to reference scanning settings such as tube voltage or tube current, presence, type, or amount of contrast agent(s), type and/or number of bowtie filters employed, type of image reconstruction software used or reconstruction technique employed, or the like. The scanning technique may correspond to reference display settings such as window level, window width, or the like. Further still, the scanning technique may also be associated with a reference image having image characteristics that may be identified, for example as discussed herein in connection with step 104 of the method 100. Thus, the reference scanning technique may be used to help define or describe an image quality, appearance, or characteristic that is expected, required, preferred, desired, or the like by a practitioner. For example, one or more image appearance qualities or characteristics may be identified via use of a histogram depicting or describing a distribution of pixels along a range of available shades in a reference displayed image. Identification of a scanning technique using or corresponding to a user input may help identify an image appearance expected or preferred by user, and can be used so that any adjustments to scanning parameters that may affect the appearance of a displayed image may be accounted for by a corresponding adjustment to display parameters so that a practitioner expectation regarding image appearance is met or satisfied.

The scanning technique may be identified based, for example, on a user input, a determination made autonomously in response to a user input, or a combination thereof. For example, a user may identify or otherwise input a reference protocol (or a type of scan corresponding to the reference protocol), with the reference protocol including corresponding values identified for scanning parameter such as tube voltage, tube current, or the like as well as display parameters such as window level, window width, or the like. A reference protocol may be provided as an industry standard or other type that may be shared among users, or may be tailored or customized for a particular user or group of users. In various embodiments, the user input may be input via use of a keypad, dial, touchscreen, or the like that allows a user to specify a particular value of a given parameter, such as voltage, current, noise index, or the like. Alternatively or additionally, a user may be presented with a series of values for a particular parameter from which a selected value may be chosen. For example, a user may be presented with a choice between various tube voltage settings or stations.

At 204, a scanning mode of operation is identified. Generally, the mode of operation may include or specify one or more factors or parameters that may influence the relationship between a change in image appearance and a change in one or more scanning parameters used to acquire scanning information and/or reconstruct an image using the acquired scanning information. The scanning mode of operation may correspond to, for example a clinical task, clinical application, or the like, to be performed and/or particular aspects of or associated with the clinical task to be performed. The mode of operation may include, specify, or otherwise correspond to one or more of a type of tissue to be scanned, a type of tissue within a scanned region to be analyzed, a portion of the body to be scanned, a type of information to be acquired via the scan and/or the purpose of a scan (such as an angiogram, or, as another example, the identification or analysis of a lesion), an indication of whether or not contrast agent is used, a type of contrast agent used, an amount of contrast agent used, or the like. The scanning mode of operation and/or scanning reference technique may be identified directly or directly using information input by a practitioner.

The scanning mode of operation may be identified, for example, at the same time that a reference scanning technique is identified via the entry or identification of a protocol. A practitioner may specify (e.g., select from a list) a particular protocol (e.g., angiogram, liver scan, head injury, lesion analysis, sinus study, brain scan, chest scan, chest scan for identification of potential tumors, chest scan for identification of fluid accumulation, or the like), and the scanning mode of operation may be determined based on the specified protocol. In various embodiments, protocols may be specified at varying levels of specificity. For example, a protocol may indicate a portion of the body to be scanned, or may indicate a portion of the body to be scanned as well as the purpose of the scan.

At 206, an attenuation (e.g., attenuation associated with a region of interest being scanned) is determined. For example, a patient attenuation corresponding to or characterizing the ability or tendency of a patient (or a region of interest of a patient) to attenuate an x-ray beam directed through the patient (or region of interest) may be determined. The attenuation, for example, may be determined using information acquired during a scout scan. In other embodiments, additionally or alternatively, the attenuation may be determined using alternate techniques. For example, the attenuation may be calculated, estimated, or otherwise determined using one or more of a patient height, patient weight, patient body mass index (BMI), patient diameter, or the like.

At 208, scanning parameters are selected. In the illustrated embodiment, at least one scanning parameter differs from a scanning parameter called for by or corresponding to the scanning technique identified at 202. A scanning parameter that differs from the reference technique may be a user input deviation that is entered by a user or determined responsive to information entered by a user. For example, after entering a reference technique, a user may enter information corresponding to a patient characteristic (e.g., pediatric, geriatric, size, or the like) and a scanning system may determine a corresponding change in one or more scanning parameters, such as a reduction in tube voltage, using the patient characteristic information entered by the user. A scanning parameter may differ from the reference technique based on an autonomous adjustment. For example, a scanning system may autonomously adjust one or more scanning parameters for a given mode of operation to reduce a diagnostic dosage, such as an exposure to radiation.

Implementation of an automatically selected setting (e.g., tube current, tube voltage, type of contrast agent, amount of contrast agent, or the like) may be fully autonomous (e.g., performed without operator intervention) in some embodiments, and not fully autonomous in other. For example, a scanning setting selected or specified by a control module or the like may be presented to a practitioner via a prompt on a display or touch screen or the like. The practitioner may then have the option of choosing the automatically selected operational setting or a different operational setting. In some embodiments, the automatically selected operational setting may act as a default setting that may be overridden by intervention by a practitioner.

At 210, a scan is performed on the object. The scan may be performed using certain settings from the reference technique and certain settings adjusted or otherwise determined at 208. A contrast agent (or agents) may be introduced into the patient as part of performing the scan. The settings may include one or more of a tube voltage, tube current, contrast agent (presence, type, and/or amount), or the like. Scanning information or data may be acquired during the scan from a detector upon which x-rays impinge after passing through the object.

At 212, an image is reconstructed. The image corresponds to the object (e.g., patient) being scanned, and may be reconstructed using scanning information or data obtained during performance of the scan at 210. The image, for example, may include a plurality of pixels, with each pixel having associated therewith a measure of contrast or brightness, such as a CT number or Hounsfield Unit (HU).

At 214, one or more display parameters are determined for display of the image reconstructed at 212. The display parameters may be determined in a generally similar fashion as discussed above in connection with step 108 of the method 100 discussed herein. The display parameters, for example, may be determined based on one or more reference scanning parameters and one or more scanning parameters used to obtain an image that differ from the reference scanning parameters. In the depicted embodiment, one or more display parameters are selected or determined so that the image displayed to a user may be displayed appearing more similar to the reference image than if the image were displayed using the one or more reference display parameters. Examples of display parameters include window level, window width, or the like.

At 216 the display parameters are used to provide a user with a viewable display of the second image (e.g., an image reconstructed at 212.) The viewable or displayed image may be provided as one or more of a display on a computer or other screen, a printout, or the like.

Thus, embodiments disclosed herein provide for improved ease of use, automatic selection of one or more display parameters (e.g., window level, window width, or the like), and improved consistency of presentation of scanning results to practitioners. For example, as discussed herein, a practitioner may input a reference setting corresponding to an established protocol. Systems and methods of various embodiments discussed herein provide for automatic adjustment of one or more display settings to account for changes to one or more scanning parameters that may have deviated from a reference value for performance of a scan, allowing scanning parameters to be adjusted while still providing an image having an overall appearance that conforms to practitioner expectations, preferences, requirements, or the like.

Figure 3:
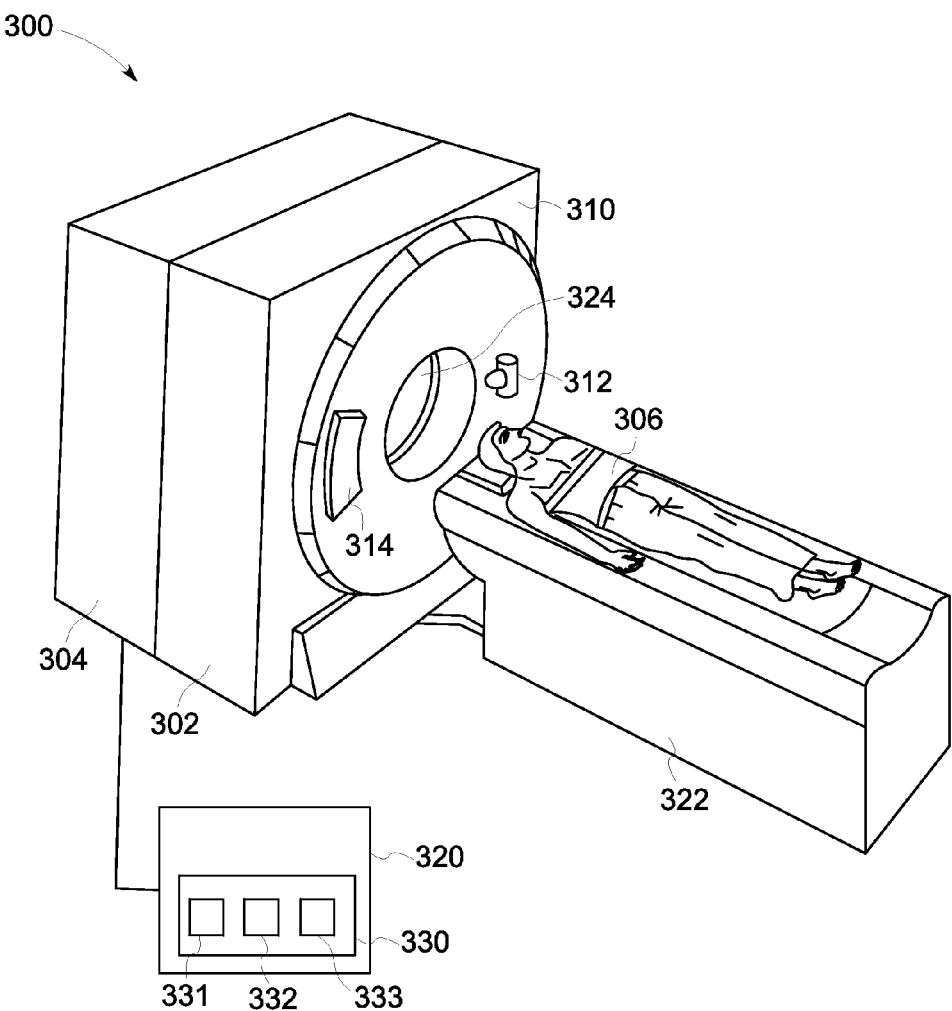
FIG. 3 is a pictorial view of an exemplary imaging system formed in accordance with various embodiments.

Various methods and algorithms described herein are used to select display settings for an image, and may be embodied as a set of instructions that are stored on a computer and implemented using, for example, a module 330, shown in FIG. 3, software, hardware, a combination thereof, and/or a tangible non-transitory computer readable medium. In one embodiment, a tangible non-transitory computer readable medium excludes signals.

Figure 4:
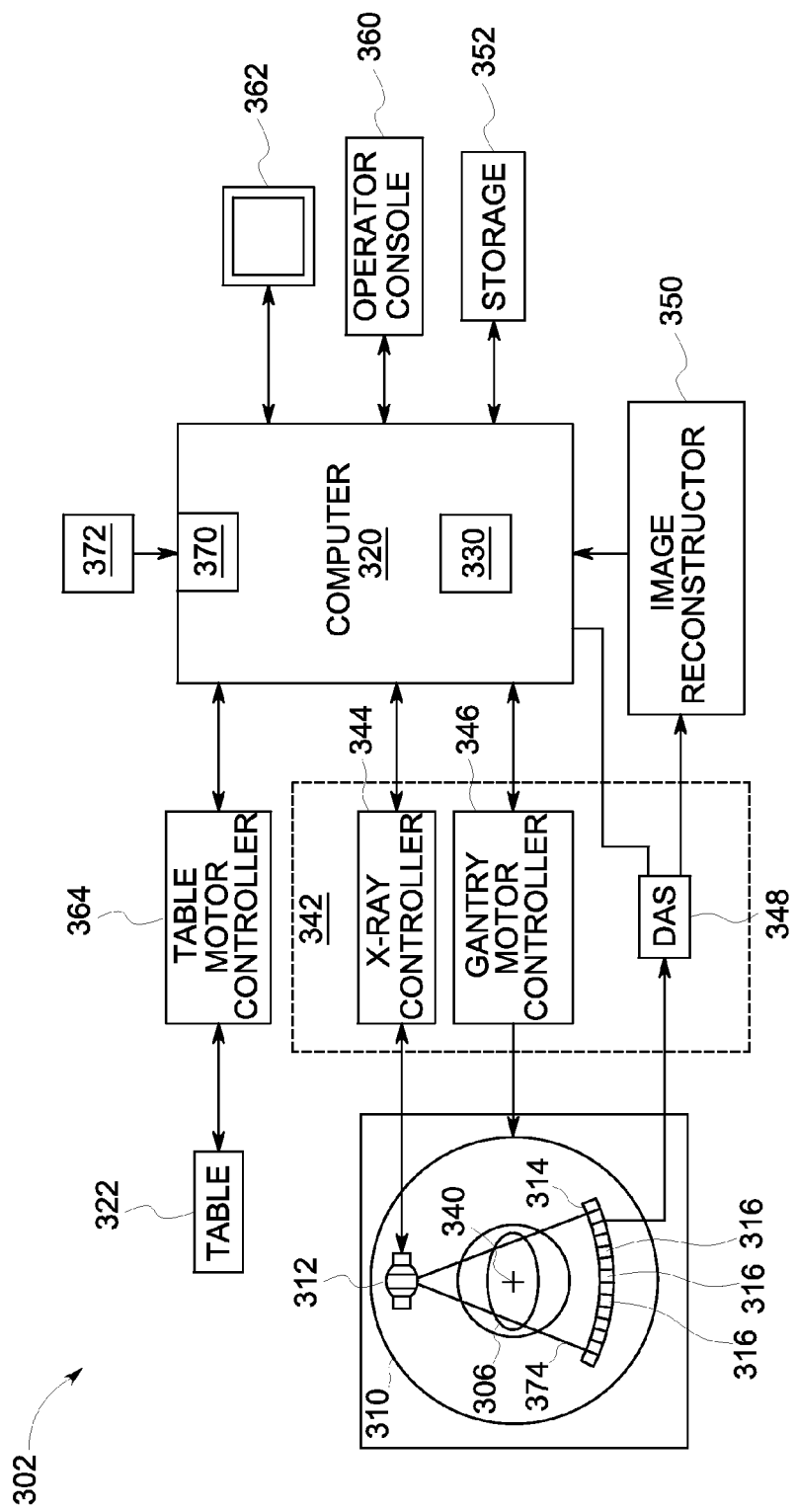
FIG. 4 is a block schematic diagram of the system illustrated in FIG. 3.

FIG. 3 is a pictorial view of an exemplary imaging system 300 that is formed in accordance with various embodiments. FIG. 4 is a block schematic diagram of a portion of the multi-modality imaging system 300 shown in FIG. 3. The imaging system may be embodied as a computed tomography (CT) imaging system, a positron emission tomography (PET) imaging system, a magnetic resonance imaging (MRI) system, an ultrasound imaging system, an x-ray imaging system, a single photon emission computed tomography (SPECT) imaging system, an interventional C-Arm tomography imaging system, a CT system for a dedicated purpose such as extremity or breast scanning, and combinations thereof, among others. In the exemplary embodiment, the system 300 is described with respect to a CT imaging system.

Although various embodiments are described in the context of an exemplary dual modality imaging system that includes a computed tomography (CT) imaging system and a positron emission tomography (PET) imaging system, it should be understood that other imaging systems capable of performing the functions described herein are contemplated as being used. Moreover, the various methods described herein may be implemented with a stand-alone CT imaging system.

A multi-modality imaging system 300 is illustrated, and includes a CT imaging system 302 and a PET imaging system 304. The imaging system 300 allows for multiple scans in different modalities to facilitate an increased diagnostic capability over single modality systems. In one embodiment, the exemplary multi-modality imaging system 300 is a CT/PET imaging system 300. Optionally, modalities other than CT and PET are employed with the imaging system 300. For example, the imaging system 300 may be a standalone CT imaging system, a standalone PET imaging system, a magnetic resonance imaging (MRI) system, an ultrasound imaging system, an x-ray imaging system, and/or a single photon emission computed tomography (SPECT) imaging system, interventional C-Arm tomography, CT systems for a dedicated purpose such as extremity or breast scanning, and combinations thereof, among others.

The CT imaging system 302 includes a gantry 310 that has an x-ray source 312 that projects a beam of x-rays toward a detector array 314 on the opposite side of the gantry 310. The detector array 314 includes a plurality of detector elements 316 that are arranged in rows and channels that together sense the projected x-rays that pass through an object, such as the subject 306. The imaging system 300 also includes a computer 320 that receives the projection data from the detector array 314 and processes the projection data to reconstruct an image of the subject 306. In operation, operator supplied commands and parameters are used by the computer 320 to provide control signals and information to reposition a motorized table 322. More specifically, the motorized table 322 is utilized to move the subject 306 into and out of the gantry 310. Particularly, the table 322 moves at least a portion of the subject 306 through a gantry opening 324 that extends through the gantry 310.

The imaging system 300 also includes a module 330 that is configured to implement various methods and algorithms described herein. The module 330 may be implemented as a piece of hardware that is installed in the computer 320. Optionally, the module 330 may be implemented as a set of instructions that are installed on the computer 320. The set of instructions may be stand-alone programs, may be incorporated as subroutines in an operating system installed on the computer 320, may be functions in an installed software package on the computer 320, and the like. It should be understood that the various embodiments are not limited to the arrangements and instrumentality shown in the drawings. In the illustrated embodiment, the module 330 includes an identification module 331, a determination module 332, and a display module 333. It may be noted that the modules 331, 332, 333 may be stand-alone units, may be incorporated as sub-modules into a single module (e.g., module 330), or one or more aspects of one or more of the modules 331, 332, 333 may be combined with or integrated with other modules as a consolidated unit or unit, or may split among separate hardware units.

In the illustrated embodiment, the identification module 331 is configured to identify one or more first scanning parameters and one or more first display parameters corresponding to a first image corresponding to a first scan. For example, the one or more first scanning parameters may include parameters that relate to the operation of equipment in obtaining scanning information. Such parameters may include tube voltage (including a projected monochromatic tube voltage), tube current, parameters indicating the presence, type, and/or amount of contrast agent, or the like. The one or more first display parameters may include parameters that relate to settings used in displaying the first image. The first image may be displayed on one or more of a screen, printout, or the like. The first display parameters may include a window level (e.g., an identification of a midpoint of a window along a contrast or brightness scale), a window width, or the like. For example, the first image may be a reference image that corresponds to a reference protocol. The first image may be an image that has been obtained using parameters as specified by a given protocol (e.g., a head scan, abdominal scan, or the like). The one or more first scanning parameters may correspond to reference scanning parameters corresponding to the reference protocol, and the one or more first display parameters may correspond to the reference protocol as well. For example a reference protocol may specify a tube voltage and tube current at which a scan is to be obtained pursuant to the reference protocol, as well as a window width and window level at which a resulting image is to be displayed. In some embodiments, the identification module 331 may identify scanning and display parameters using input from a practitioner. For example, a practitioner may provide one or more parameters via entry into the operator console 360. As another example, a reference protocol may be entered by a practitioner using the operator console 360, with the identification module 331 configured to identify parameters based on the reference protocol.

The identification module 331 depicted in FIG. 3 is further configured to identify one or more second scanning parameters corresponding to scanning information acquired during a second scan. The second scanning parameters may include tube voltage (including a projected monochromatic tube voltage), tube current, parameters indicating the presence, type, and/or amount of contrast agent, or the like. The second scanning parameters may differ from corresponding first parameters of the first (e.g., reference) scan. For example, the second scanning parameters may include a tube voltage and/or a tube current that differs from a corresponding value for a first scan. In some embodiments, one or more of the scanning parameters may have been adjusted automatically. For example, a practitioner may provide, via user input, a reference protocol calling for a particular tube current or voltage. One or more modules of the imaging system 300 may then automatically adjust the tube current and/or voltage, for example to reduce a dosage of radiation received by a patient being scanned. Alternatively or additionally, one or more of the scanning parameters may have been adjusted by a practitioner. For example, a practitioner may provide user input altering one or more scanning parameters from a reference level to reduce a tube voltage for a scan to be performed on a patient substantially smaller than average size (e.g., a child or infant).

The determination module 332 of the illustrated embodiment is configured to determine, based on the one or more first scanning parameters and the one or more second scanning parameters, one or more second display parameters so that the scanning information acquired during the second scan may be used to provide a second image appearing more similar to the first image than if the second image were displayed using the one or more first display parameters. For example, if a user has input a reference protocol calling for a scan to be performed using the first scanning parameters and the first display parameters, the user may have an expectation of how the resulting image will appear. Such an expectation may include one or more of an overall appearance, a level of contrast or brightness, a number and/or distribution of shades or gradations of a color (e.g., grey), an amount of distinctiveness between shades or gradations of a color, or the like. However, for a scan that is performed using second scanning parameters that differ from the first scanning parameters, if the same display parameters (e.g., the first display parameters) are used to display the resulting image, the user's expectation may not be satisfied, even if the resulting image is considered acceptable using one or more image quality metrics (e.g., CNR). The determination module 332 is configured to determine second display parameters selected to present an image resulting from a scan taken using the second scanning parameters so that the image appears similar (or more similar) to an image that would result from a scan taken using the first scanning parameters and displayed using the first display parameters. In the illustrated embodiment, the determination module 332 determines the second display parameters using the first and second scanning parameters.

For example, the determination module 332 may determine an adjustment to be made to one or more first display parameters to provide one or more second display parameters. In some embodiments, the first display parameters may include a first window level and a first window width, and the second display parameters may include a second window level and a second window width. The determination module 332 may determine the second window level using the first window level adjusted by an amount corresponding to a difference between one or more first and second scanning parameters. For example, the determination module 332 may determine the second window level by adjusting the first window level by an amount corresponding to a difference between a first tube voltage corresponding to the first image and a second tube voltage corresponding to the second image. Similarly, the determination module 332 may determine the second window width using the first window width adjusted by an amount corresponding to a difference between one or more first and second scanning parameters. For example, the determination module 332 may determine the second window width by adjusting the first window width by an amount corresponding to a difference between a first tube current corresponding to the first image and a second tube current corresponding to the second image.

In the illustrated embodiment, the display module 333 is configured to use the one or more second display parameters (e.g., determined by the determination module 332) to provide the second image configured to be displayed to a viewer. For example, the display module 33 may provide the visual display unit 362 with settings, instructions, or the like to display an image (e.g., an image reconstructed using scanning information collected during a scan performed using the second scanning parameters). The one or more second display parameters may include, for example, a window level, a window width, or the like. In some embodiments, the image may be displayed to a viewer on a screen. Alternatively or additionally, the image may be displayed to a viewer as a printout.

As discussed above, the detector 314 includes a plurality of detector elements 316. Each detector element 316 produces an electrical signal, or output, that represents the intensity of an impinging x-ray beam and hence allows estimation of the attenuation of the beam as it passes through the subject 306. During a scan to acquire the x-ray projection data, the gantry 310 and the components mounted thereon rotate about a center of rotation 340. FIG. 4 shows only a single row of detector elements 316 (i.e., a detector row). However, the multislice detector array 314 includes a plurality of parallel detector rows of detector elements 316 such that projection data corresponding to a plurality of slices can be acquired simultaneously during a scan.

Rotation of the gantry 310 and the operation of the x-ray source 312 are governed by a control mechanism 342. The control mechanism 342 includes an x-ray controller 344 that provides power and timing signals to the x-ray source 312 and a gantry motor controller 346 that controls the rotational speed and position of the gantry 310. A data acquisition system (DAS) 348 in the control mechanism 342 samples analog data from detector elements 316 and converts the data to digital signals for subsequent processing. For example, the subsequent processing may include utilizing the module 330 to implement the various methods described herein. An image reconstructor 350 receives the sampled and digitized x-ray data from the DAS 348 and performs high-speed image reconstruction. The reconstructed images are input to the computer 320 that stores the image in a storage device 352. Optionally, the computer 320 may receive the sampled and digitized x-ray data from the DAS 348 and perform various methods described herein using the module 330. The computer 320 also receives commands and scanning parameters from an operator via a console 360 that has a keyboard. An associated visual display unit 362 allows the operator to observe the reconstructed image and other data from the computer 320. The operator supplied commands and parameters are used by the computer 320 to provide control signals and information to the DAS 348, the x-ray controller 344 and the gantry motor controller 346. In addition, the computer 320 operates a table motor controller 364 that controls the motorized table 322 to position the subject 306 in the gantry 310. Particularly, the table 322 moves at least a portion of the subject 306 through the gantry opening 324 as shown in FIG. 3.

Referring again to FIG. 4, in one embodiment, the computer 320 includes a device 370, for example, a solid-state drive, flash drive, CD-ROM drive, DVD drive, magnetic optical disk (MOD) device, or any other digital device including a network connecting device such as an Ethernet device for reading instructions and/or data from a computer-readable medium 372, such as a CD-ROM, a DVD or another digital source such as a network or the Internet, as well as yet to be developed digital means. In another embodiment, the computer 320 executes instructions stored in firmware (not shown). The computer 320 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

In the exemplary embodiment, the x-ray source 312 and the detector array 314 are rotated with the gantry 310 within the imaging plane and around the subject 306 to be imaged such that the angle at which an x-ray beam 374 intersects the subject 306 constantly changes. A group of x-ray attenuation measurements, i.e., projection data, from the detector array 314 at one gantry angle is referred to as a "view". A "scan" of the subject 306 comprises a set of views made at different gantry angles, or view angles, during one revolution of the x-ray source 312 and the detector 314. In a CT scan, the projection data is processed to reconstruct an image that corresponds to a two dimensional slice taken through the subject 306.

Exemplary embodiments of a multi-modality imaging system are described above in detail. The multi-modality imaging system components illustrated are not limited to the specific embodiments described herein, but rather, components of each multi-modality imaging system may be utilized independently and separately from other components described herein. For example, the multi-modality imaging system components described above may also be used in combination with other imaging systems. As another example, single modality systems may be employed in some embodiments.

Thus, embodiments discussed herein provide for a reduction or minimization of a potentially harmful, inconvenient, expensive, or otherwise undesirable diagnostic dosage, improved ease of use of tube voltage selection, automatic selection or adjustment of tube voltage and/or current to reduce or minimize diagnostic dosage, and/or the automatic selection of imaging parameters to produce a reconstructed image having an image quality tailored for particular practitioners.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid state drive, optical drive, and/or the like. The storage device may also be other similar means for loading computer programs or other instructions into the computer or processor.

As used herein, the term "computer" may include any processor-based or microprocessor-based system including systems using microcontrollers, reduced instruction set computers (RISC), application specific integrated circuits (ASICs), logic circuits, GPUs, FPGAs, and any other circuit or processor capable of executing the functions described herein. The above examples are exemplary only, and are thus not intended to limit in any way the definition and/or meaning of the term "computer". The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software, which may be a tangible and non-transitory computer readable medium. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the phrase "reconstructing an image" is not intended to exclude embodiments of the present invention in which data representing an image is generated, but a viewable image is not. Therefore, as used herein the term "image" broadly refers to both viewable images and data representing a viewable image. However, many embodiments generate, or are configured to generate, at least one viewable image.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. An imaging system comprising:
   an identification module configured to identify one or more first scanning parameters and one or more first display parameters corresponding to a first image, the identification module also configured to identify one or more second scanning parameters corresponding to scanning information acquired during a second scan;
   a determination module configured to determine, based on the one or more first scanning parameters and the one or more second scanning parameters, one or more second display parameters used to display a second image, wherein the second image is displayed having an apparent image quality more similar to an apparent image quality of the first image than if displayed using the one or more first display parameters; and
   a display module configured to use the one or more second display parameters to provide the second image configured to be displayed to a viewer.

2. The imaging system of claim 1, wherein the first image is a reference image corresponding to a reference protocol, the one or more first scanning parameters are reference scanning parameters corresponding to the reference protocol, and the one or more first display parameters correspond to the reference protocol.

3. The imaging system of claim 2, wherein the determination module is configured to determine an adjustment to be made to the one or more first display parameters to provide the one or more second display parameters.

4. The imaging system of claim 1, wherein the one or more first scanning parameters correspond to a user input, and wherein the one or more second scanning parameters comprise an automatically adjusted scanning parameter that has been automatically adjusted from one of the one or more first scanning parameters.

5. The imaging system of claim 4, wherein the automatically adjusted scanning parameter comprises a tube voltage setting.

6. The imaging system of claim 1, wherein the one or more first scanning parameters corresponds to a reference protocol, and wherein the one or more second scanning parameters comprise a scanning parameter that corresponds to a user input deviation from the reference protocol.

7. The imaging system of claim 1, wherein the one or more first display parameters comprises at least one of a window width or a window level, and wherein the one or more second display parameters comprises at least one of a window width or a window level.

8. The imaging system of claim 1, wherein the one or more first scanning parameters comprises a first tube voltage, the one or more second scanning parameters comprises a second tube voltage, the one or more first display parameters comprises a first window level, and the one or more second display parameters comprises a second window level, and wherein the determination module is configured to determine the second window level by adjusting the first window level an amount corresponding to a difference between the first tube voltage and the second tube voltage.

9. The imaging system of claim 1, wherein the one or more first scanning parameters comprises a first tube current, the one or more second scanning parameters comprises a second tube current, the one or more first display parameters comprises a first window width, and the one or more second display parameters comprises a second window width, and wherein the determination module is configured to determine the second window width by adjusting the first window width an amount corresponding to a difference between the first tube current and the second tube current.

10. The imaging system of claim 1, wherein the one or more first scanning parameters comprises a first tube voltage and a first tube current, the one or more second scanning parameters comprises a second tube voltage and a second tube current, the one or more first display parameters comprises a first window level and first window width, and the one or more second display parameters comprises a second window level and a second window width, and wherein the determination module is configured to determine the second window level by adjusting the first window level an amount corresponding to a difference between the first tube voltage and the second tube voltage and to determine the second window width by adjusting the first window width an amount corresponding to a difference between the first tube current and the second tube current.

11. The imaging system of claim 1, wherein the first image is a theoretical construct that is not actually acquired, reconstructed, or displayed.

12. A method for displaying results of a scan comprising:
identifying one or more reference scanning parameters and one or more reference display parameters corresponding to a reference image for a reference scan;
identifying one or more second scanning parameters corresponding to scanning information acquired during a second scan;
determining, based on the one or more reference scanning parameters and the one or more second scanning parameters, one or more second display parameters used to display the second image, wherein the second image is displayed having an apparent image quality more similar to an apparent image quality of the first image than if displayed using the one or more first display parameters; and
using the one or more second display parameters to provide the second image configured to be displayed to a viewer.

13. The method of claim 12, further comprising determining an adjustment to be made to the one or more first display parameters to provide the one or more second display parameters.

14. The method of claim 12, wherein the one or more reference scanning parameters correspond to a user input, the method further comprising automatically determining the one or more second scanning parameters based off an adjustment to the one or more reference scanning parameters.

15. The method of claim 12, wherein the one or more reference display parameters comprises at least one of a window width or a window level, and wherein the one or more second display parameters comprises at least one of a window width or a window level.

16. The method of claim 12, wherein the one or more reference scanning parameters comprises a reference tube voltage, the one or more second scanning parameters comprises a second tube voltage, the one or more reference display parameters comprises a reference window level, and the one or more second display parameters comprises a second window level, the method further comprising determining the second window level by adjusting the reference window level an amount corresponding to a difference between the reference tube voltage and the second tube voltage.

17. The method of claim 12, wherein the one or more reference scanning parameters comprises a reference tube current, the one or more second scanning parameters comprises a second tube current, the one or more reference display parameters comprises a reference window width, and the one or more second display parameters comprises a second window width, the method further comprising determining the second window width by adjusting the reference window width an amount corresponding to a difference between the reference tube current and the second tube current.

18. A tangible and non-transitory computer readable medium comprising one or more computer software modules configured to direct a processor to:
identify one or more reference scanning parameters and one or more reference display parameters corresponding to a reference image for a reference scan;
identify one or more second scanning parameters corresponding to scanning information acquired during a second scan;
determine, based on the one or more reference scanning parameters and the one or more second scanning parameters, one or more second display parameters used to display the second image, wherein the second image is displayed having an apparent image quality more similar to an apparent image quality of the first image than if displayed using the one or more first display parameters; and
use the one or more second display parameters to provide the second image configured to be displayed to a viewer.

19. The tangible and non-transitory computer readable medium of claim 18, wherein the one or more reference display parameters comprises at least one of a window width or a window level, and wherein the one or more second display parameters comprises at least one of a window width or a window level.

20. The tangible and non-transitory computer readable medium of claim 18, wherein the one or more reference scanning parameters comprises a reference tube voltage, the one or more second scanning parameters comprises a second tube voltage, the one or more reference display parameters comprises a reference window level, and the one or more second display parameters comprises a second window level, wherein the one or more software modules are further configured to direct the processor to determine the second window level by adjusting the reference window level an amount corresponding to a difference between the reference tube voltage and the second tube voltage.

21. The tangible and non-transitory computer readable medium of claim 18, wherein the one or more reference scanning parameters comprises a reference tube current, the one or more second scanning parameters comprises a second tube current, the one or more reference display parameters comprises a reference window width, and the one or more second display parameters comprises a second window width, wherein the one or more software modules are further configured to direct the processor to determine the second window width by adjusting the reference window width an amount corresponding to a difference between the reference tube current and the second tube current.

\* \* \* \* \*